United States Patent [19]

Healy et al.

[11] 4,051,522
[45] Sept. 27, 1977

[54] PATIENT MONITORING SYSTEM

[75] Inventors: James W. Healy, Malibu; Bob L. Currier, Gardena, both of Calif.

[73] Assignee: Jonathan Systems, Los Angeles, Calif.

[21] Appl. No.: 574,315

[22] Filed: May 5, 1975

[51] Int. Cl.² .............................................. H04N 7/18
[52] U.S. Cl. ................................. 358/86; 128/2.1 A; 340/324 AD; 358/93; 358/142; 358/181
[58] Field of Search ..................... 178/6.8, DIG. 13; 340/324 AD; 128/2.1 A; 312/7, 204, 209, 210, 242, 7; 325/352, 353; 343/225, 228; 358/86, 93, 142, 181

[56] References Cited
U.S. PATENT DOCUMENTS

| | | | |
|---|---|---|---|
| 2,282,384 | 5/1942 | Schenck | 325/352 |
| 2,938,113 | 5/1960 | Schnell | 325/352 |
| 3,588,336 | 6/1971 | Scher | 178/DIG. 13 |
| 3,613,669 | 10/1971 | Corbin | 128/2.1 A |
| 3,646,606 | 2/1972 | Buxton | 128/2.1 A |
| 3,659,283 | 4/1972 | Ophir | 340/324 A |
| 3,765,009 | 10/1973 | Graves | 340/324 A |
| 3,910,257 | 10/1975 | Fletcher | 128/2.1 A |

Primary Examiner—Howard W. Britton
Attorney, Agent, or Firm—John E. Wagner

[57] ABSTRACT

Disclosed is a hospital patient monitoring and display system employing a number of bedside consoles, concealable from the patient and including input for various patient sensors such as ECG, pulse rate, patient temperature and blood pressure. The consoles are powered by a low voltage direct current supply at a central station. The central station includes signal processing and display apparatus to allow the patient data to be displayed on a conventional commercial black and white or color television set along with alpha numerics related to each respective patient. The display is coupled to the hospitals normal entertainment television distribution network, if any, allowing the patient data to be displayed on any television set throughout the hospital. The signal processing and display portions of the system include a control to vary the trace speed and to freeze a display. A printer is connected to the display system to automatically print a reproduction of the display whenever the "freeze" control is actuated. A remote control operation via a radio frequency link may be carried by a patient's doctor and may be operated at any time or place within reception range of the central control to freeze the display for better examination and automatic printout of a reproduction. After a preset period, the display resumes.

The system includes controls for setting maximum allowable values of various parameters and for sounding an alarm whenever the patient parameter varies from the allowable value. Such variation is registered as a shift from one color display to a different one in the case of color television sets, e.g. normal trace, green and abnormality, red. In the case of black and white displays, an alarm condition may be represented as intensity modulation or flashing of the display.

5 Claims, 8 Drawing Figures

FIG 6
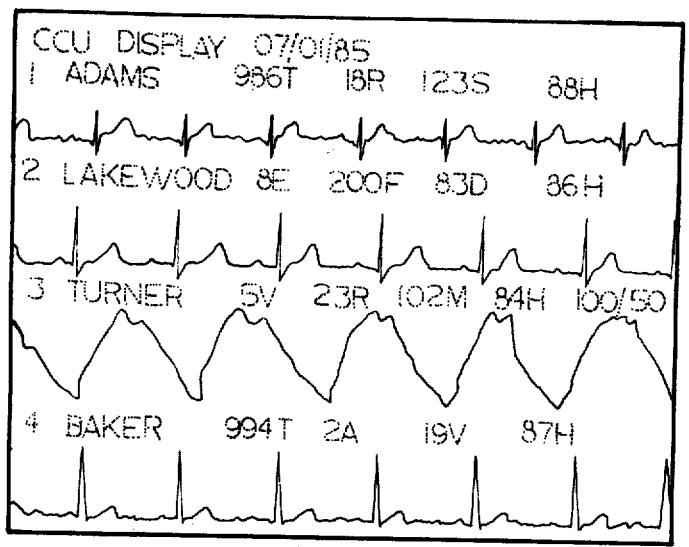
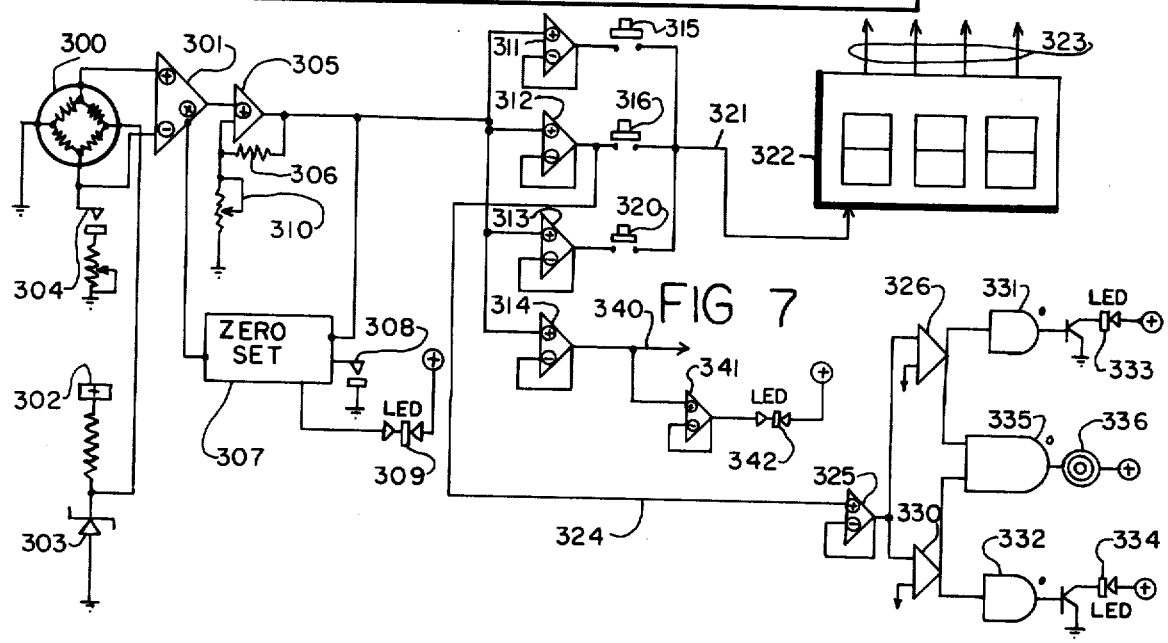
FIG 7

PATIENT MONITORING SYSTEM

BACKGROUND OF THE INVENTION

Classically, hospital patient monitoring systems have involved the use of patient sensors connected to local signal processors powered by standard power mains (115 volts AC) and connected via communications cables to a central system for display. Typically, such displays have been medical cardioscopes and other specialized displays.

One of the major limitations on such systems is the need of each patient station to provide absolute isolation between the 115 volt AC supply and the patient to whom a few microamperes of leakage current may prove fatal. Extensive patient isolation apparatus has therefore been absolutely mandatary for each bed.

One of the other limitations is the specialized displays being expensive, are usually available only at the patient monitoring station where they are grouped for monitoring by one or more attendants. An alarm condition of one of several patients is difficult to visually and audably isolate and in general is extremely difficult to monitor effectively.

A number of patents illustrate systems of the above type. Representative are:

| | | |
|---|---|---|
| 3,690,312 | B. H. Weppner et al | Sept. 12, 1972 |
| 3,779,237 | R. R. Goelte et al | Dec. 18, 1973 |
| 3,536,062 | A. J. Horn | Oct. 27, 1970 |
| 3,545,429 | E. R. Penta et al | Dec. 8, 1970 |
| 3,584,618 | C. J. Reinhard et al | June 5, 1971 |

Certain patents have disclosed the use of radio frequency links in patient telemetry systems either between the patient and a local antenna or between the patient and a central monitoring station.

Such patents are:

| | | |
|---|---|---|
| 3,638,642 | A. E. Heflin Sr. | Feb. 1, 1972 |
| 3,646,606 | R. L. Buxton et al | Feb. 29, 1972 |
| 3,603,881 | W. E. Thornton | Sept. 7, 1971 |
| 3,639,907 | W. Greatbach | Feb. 1, 1972 |

A patent disclosing the use of conventional commercial television sets for display of patient monitoring data is:

| | | |
|---|---|---|
| 3,530,236 | A. R. Marko | Sept. 22, 1970. |

It has also been proposed in one publication, namely Biophysical Measurements, by Peter Strong, published in November, 1970 by Tectronix, Inc. that low cost television sets may be employed for display of patient data throughout a hospital. It was suggested therein that an alarm condition could be made to trigger a recorder to produce a permanent record of the patient data.

BRIEF DESCRIPTION OF THE INVENTION

We have produced a patient monitoring system employing low voltage patient bedside consoles and a central, isolated power supply, signal processing and display station. The displays are conventional television sets, color or black and white and connected to the system through the normal television distribution system. Unused entertainment channels may be used for patient data display.

The system includes a patient station totally mounted in the wall at patient bedside and concealed when not in use by an attractive framed picture which is removable to allow use of the patient station. All power to the patient station is low voltage which is isolated at the central power supply from the A.C. mains. Further isolation occurs at the patient station.

Each patient station is designed to mount up to four modules depending upon the particular needs of the hospital or the particular patient and each station includes local outputs for T.V., oscilloscope, computer or recorder. Each patient station is connected to the power supply and central station by simple twisted pair or coaxial of communications type cabling.

One feature of this invention involves a presence of a non-fade display of patient data in a video format. Another feature of this invention involves a manual control to freeze the present display and to automatically print out a permanent record of the display each time the freeze control is actuated.

Still another feature of this invention involves a remote controllable radio frequency link to the central control station allowing the patient's doctor to freeze and print out a record of a present display from any place within range of the remote video link.

One other feature involves the provision for superimposing of pictorial and alpha numeric information whereby X-rays and other pictorial displays may be presented, for example, to an operating surgeon, immediately upon processing at the X-ray laboratory along with patient identification information.

BRIEF DESCRIPTION OF THE DRAWING

The above features of this invention may be more clearly understood by the following detailed description and by reference to the drawings in which:

FIG. 3 is a more detailed block diagram of this invention;

FIG. 6 is a graphical display in accordance with this display;

FIG. 7 is an electrical schematic diagram of a patient amplifier module in accordance with this invention.

DETAILED DISCLOSURE OF THE INVENTION

Figures 1, 5:
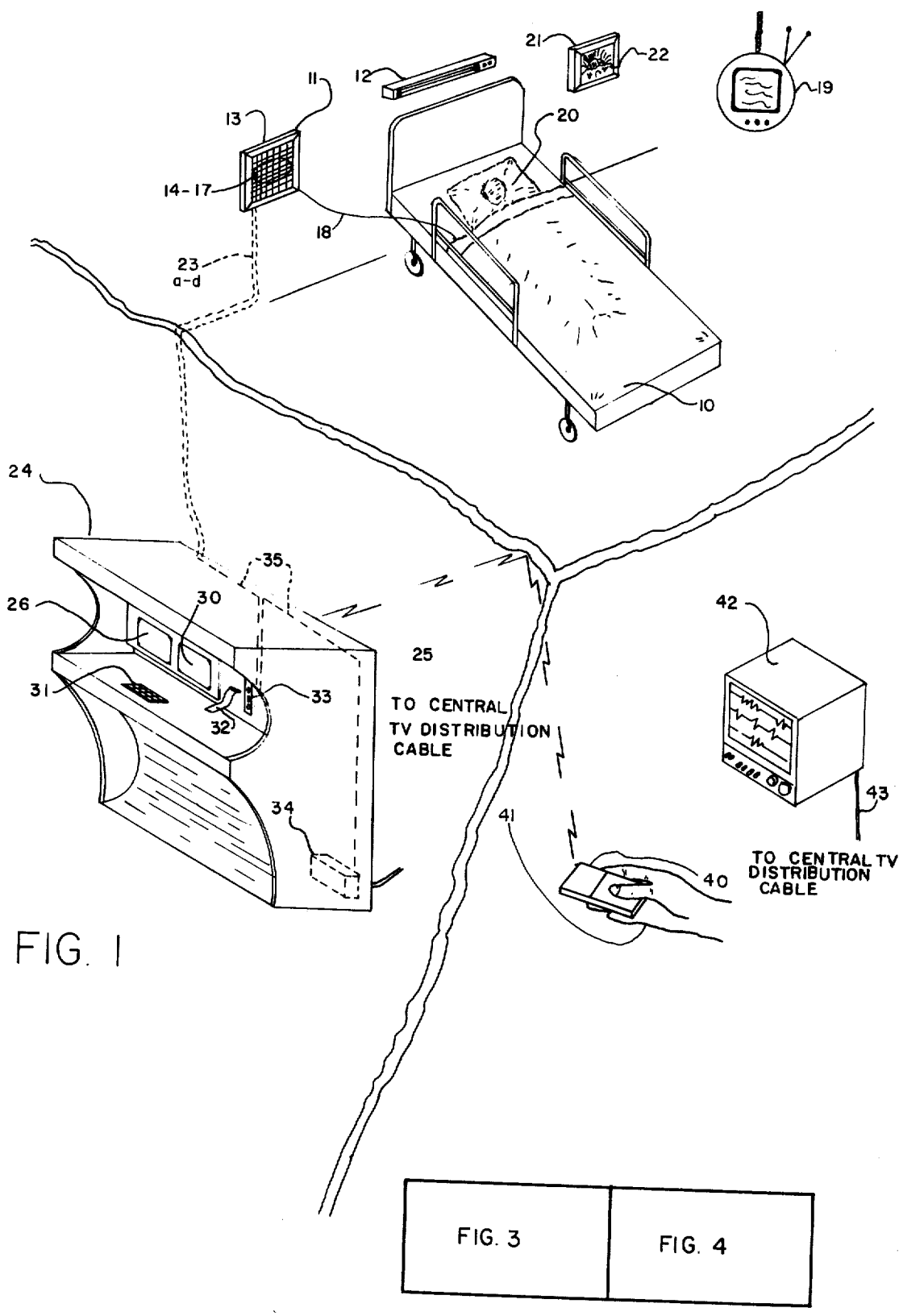
FIG. 1 is a perspective view of a hospital installation incorporating this invention.
FIG. 5 is an arrangement of FIGS. 3 and 4.
Figure 4:
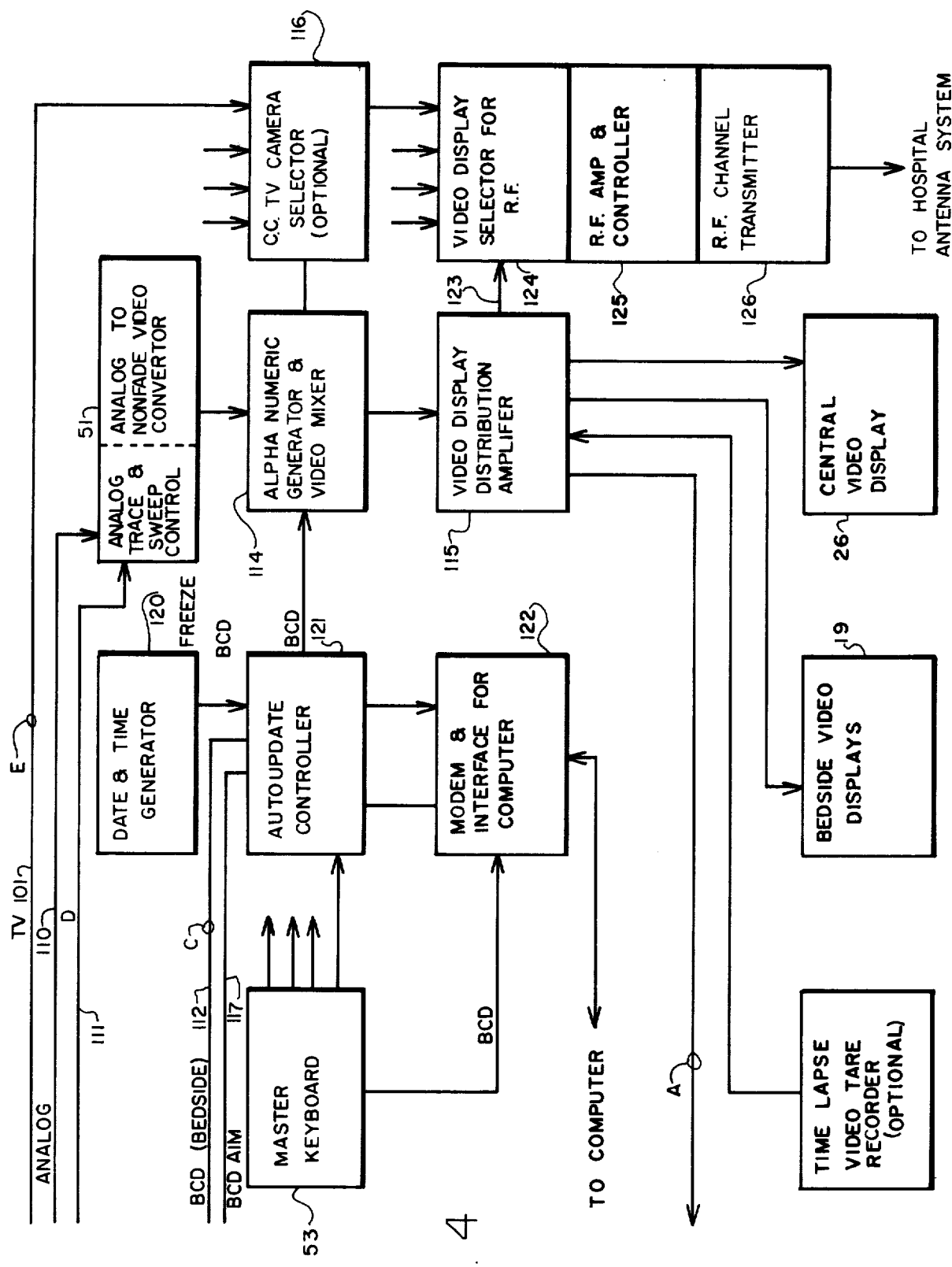
FIG. 4 is a continuation of FIG. 3.

Continuous real time monitoring of hospitalized patients has developed in the last few years to the level where every hospital must have several monitored beds in at least the intensive care and cardiac care wards. Such systems must be flexible to adapt to new types of sensors, to add to the diagnostic inputs and similarly the displays must be meaningful, unambiguous and clearly identify abnormalities in any of a number of patients without deluging the nursing staff and physicians with records of insignificant data. A need exists for real time, continuous patient data combined with alpha numerics available to monitoring nurses and to the patient's doctor on a near instantaneous basis and for permanent records of data of interest or abnormalities.

additional features better shown in FIGS. 3 and 4. In these figures, identical elements to FIGS. 1 and 2 employ identical reference numerals. FIGS. 3 and 4 are arranged as shown in FIG. 5.

Now referring to FIGS. 3 and 4, the bedside station for a four bed installation includes, in addition to the cabinets 13a-d, an optional closed circuit television camera 100 directed toward the cabinets 13a-d or the patients for direct live monitoring of the bedside conditions over leads 101. Analog patient data from the sensors connected to the patients from the four cabinets 13a-d are again transmitted on lead 23a-d to an interface assembly 102 or distribution panel. In this case binary coded decimal data (BCD) is additionally available from bedside modules representing such parameters as heart rate and patient temperature. These BCD signals are available where the individual modules of the cabinets 13a-d generate such signals for example, to display such parameter at the bedside in digital form. The same circuitry used to display these parameters applies to the BCD signal to lead 103 for use or display at the central control station. D.C. power for all bedside modules again is supplied over lead 23p from the central power supply 27.

In many instances the patient may be monitored via a R.F. telemetry link while wearing a telemetry transmitter 104. A telemetry receiver 105 is then connected to the leads 23 or 103 depending upon the nature of the signal from the patient. It is usually in analog form. The telemetry receiver may include counters and provision for under or over count limits, for example, upper and lower heart rate limits and transmit an alarm condition signal only. This arrangement is represented by the heart rate limit controls 106. The foregoing constitutes a novel bedside installation.

The central control console is connected to the bedside installation via the interface assembly 102. The output of the interface assembly 102 to the central console constitutes analog data on leads 110 and 111 and binary coded decimal data on leads 112 and 113. The analog signals on lead 110 are introduced into the video translator 51 which both stores the analog signal for periods of up to 120 seconds and converts it to commercial video format including synchronized horizontal and sweep signals. The lead 110 represents four leads from individual beds and these signals are all converted and placed in video format for display in vertical array on the face of a commercial display 26 in the console and at bedside displays 19 after combining in a video mixer 114 and amplification in video display distribution amplifier 115. The mixer 114 also combines the closed circuit TV input where used from a selector 116 to display bedside scenes where desired.

An even more inportant application is to display either alone or superimposed on other patient data, other information, for example, a freshly processed X-ray photograph where the camera 100 is located in the X-ray process laboratory and one monitor is at bedside or in an operating room. The surgeon may examine the X-ray while operating without any physical transfer or handling of the X-ray photograph.

The video mixer 114 also provides an additional function of importance. It receives BCD data from the master keyboard 53, lead 112 and a date and time signal generator 120 via and auto update controller 121. The keyboard allows the generation of BCD encoded alpha numeric information such as the patients name, bed or location, medication or special information. The date and time generator 120 generates BCD signals representing actual time and date. The auto update controller 120 automatically enters real time date on lead 112, data and time data from generator 120, BCD A.M. data on a lead 117, when present, and alpha numerics from keyboard 53 into the character generator portion of mixer 114 where they are combined with the analog signals. The data is combined and ultimately displayed on monitors 19 and 26 in the form represented in FIG. 6 of the drawing.

The master keyboard 53 and the auto controller 121 also constitute data sources for computer storage of patient data and thus are both connected to a modem and interface circuit 122 for interconnection with a computer, unshown in the drawing. The modem and interface circuit 122 is selected for compatability with the BCD inputs and whichever computer may be used by the hospital.

In addition to the direct cabled distribution to analog and alpha numeric data to television displays, an RF distribution link may be used. This is used by connecting the video display distribution amplifier 115 over lead 123 to a video display selector switch 124 and in turn to, to an RF amplifier 125 and RF transmitter 126. The tansmitter 126 is connected to transmitting antenna 56, unshown in FIG. 4 but appearing in FIG. 2. Closed circuit TV input from selector 116 may also be applied to the controller 124 for distribution if desired.

Employing this last feature, any commercial television set within range of the hospital antenna may display patient data as required. As examples of ultimate applications, a patient's physician may carry on other duties in the hospital while having either an AC powered or portable battery powered television set in front of him and observe real time physiological data of his patient. Where, as often is the case, a physician may have his office in the hospital or in a nearby building, he may proceed with his office schedule while continuously monitoring a critical patient. Also employing two other features of this invention this same physician may, from his remote location, be alerted to abnormalities in the patient's data and on command, have a printout of either an abnormality or any desired date produced. These features are disclosed below.

The basic control at the central control station is the central alarm selector 130 receiving power from the power supply and binary coded data from the patients bedside via interface 102 and lead 113. The nurse or operator, under the direction of the patient's physician, sets limits such as respiration rate, heart rate, blood pressure, or whatever parameter is being monitored. The selector 130 is set to provide an alarm signal on lead 131 whenever such limits are exceeded. This alarm signal is applied via interface 102, lead 112 to the auto update controller 112. When color displays are employed, the signal from the auto update controller 121 is applied to change the trace color in the mixer 114, e.g. from white to red. In the case of black and white monitors, it is used to Z modulate the trace to provide a flashing or higher intensity trace. Both may be combined, e.g. Z modulation plus color modulation. Color sets then display a color change of brighter intensity and black and white monitors, a brighter or flashing display. Central alarm selector 130 is also connected to analog recorder 32 to activate it upon any alarm condition. The recorder thus produces a record of the analog signals at the time of the alarm. Normally, the controller will reset after a preselected period and recorder 32 will stop.

| COMPONENT | MANUFACTURER & ADDRESS | MODEL |
|---|---|---|
| Telemetry transmitter 104 | Pacific Communications, Inc. Santa Ana, Calif. | System 75 |
| Telemetry receiver 105 Analog recorder 32 | Gulton Industries, Inc. East Greenwich, R.I. | Mark 3 |
| Remote control 40 single & double | Linear Corporation Inglewood, California 90301 | Genie b120 |
| Remote receiver 34 Central Arrhythma Detector | Wolff Industries San Marino, Calif. | 788 |
| Master keyboard 53 & Alpha update controller 121 | Carmel Electronics Los Angeles, Calif. | 10301-302-100 |
| R.F. Amp 125 & transmitter 126 | Catel Incorporated Mountain View, Calif. | VN 1500 |
| Mixer & video Mixer 114 and video translator 51 | Hughes Aircraft Co. Oceanside, Calif. | MSC-1 |
| Video Displays 19, 26 | any conventional TV set or monitor | |

One additional feature of this invention involves an additional RF link and control circuitry. As shown in FIG. 1, the central console 24 includes a remote receiver 34 with its antenna 35. A hand held signalling device similar to a portable garage door opener signalling device is employed. This signalling device transmits a signal whenever it is within range of the receiver 34 (e.g. 300 feet.) The receiver 34 and remote control 40 may be single or multiple channel but in either case an output signal is applied to lead 131 to the interface circuit 102 and thence to the lead 132 and freeze control of the video converter 51. Thus operation of the remote control 40 will freeze the image on all of the video monitors allowing the physician to examine the trace for the freeze period e.g. 30 seconds before the trace begins again.

The remote receiver 34, upon a freeze command, also applies a print command signal over lead 133 to video input selector 134 and a video printer 135 which prints an actual reproduction of the present face of an internal monitor. Thus the physician regardless of his location, when actuating the remote control 40 not only sees the frozen pictures at that time but upon his next stop at the control console may obtain a relatively high resolution print of the frozen picture for examination or permanent record. Where the signalling device is multichannel, its particular signal is transmitted on to the video imput selector 134 which will allow printing of only the required portion of the video display or will mark the trace of interest.

The one additional feature of this invention involves the presence of a central arrhythma detector 140, driven by analog signals on lead 111 to detect arrhythma conditions, e.g. rhythm changes of the heart. The central arrhythma detector produces, upon detection, an alarm signal in BCD format on leads 145 and 146 and as a simple alarm pulse on lead 150 to the remote receiver. The trace is then frozen on video monitors and a printout made on printer 33.

One of the features of this invention is that despite the flexibility and completeness of this system, its cost is surprisingly low since it employs conventional television sets as monitors, as compared with cardioscopes, and many of the components are off-the-shelf items, available and used without change. When combined in an integrated system, the advantages appear. Standard elements making up the system are identified below:

Now referring to FIG. 6, in which a typical display 30 of FIG. 1 is illustrated. It combines graphical representations of actual patient data with alpha numerics identifying the patient by name or bed number, date and time, vital parameters such as temperature, pulse rate, medications or any other significant data which the patient's physician may desire displayed. The data and one trace from each of a number of patients may be displayed simultaneously. A four patient display is illustrated in FIG. 6. As indicated above, the display trace rate is controllable and freezable so that rapid response data may be expanded for easier analysis by the physician. As desired above, the trace may be frozen by remote control. The display of FIG. 6 appears on the central control console of FIG. 1 and may be transmitted via unused entertainment channel to each of a number of entertainment television sets in patient rooms or in doctor's offices or lounges. Thus, the physician may see a real time display of his patients vital parameters any place where an entertainment television set is available. He may obtain a print of any interesting trace merely by operating the portable freeze control. Where the display is on a color television monitor, the normal trace may be in white and the trace converted to a distinguishable color, e.g. red, when present limits are exceeded.

Figure 2:
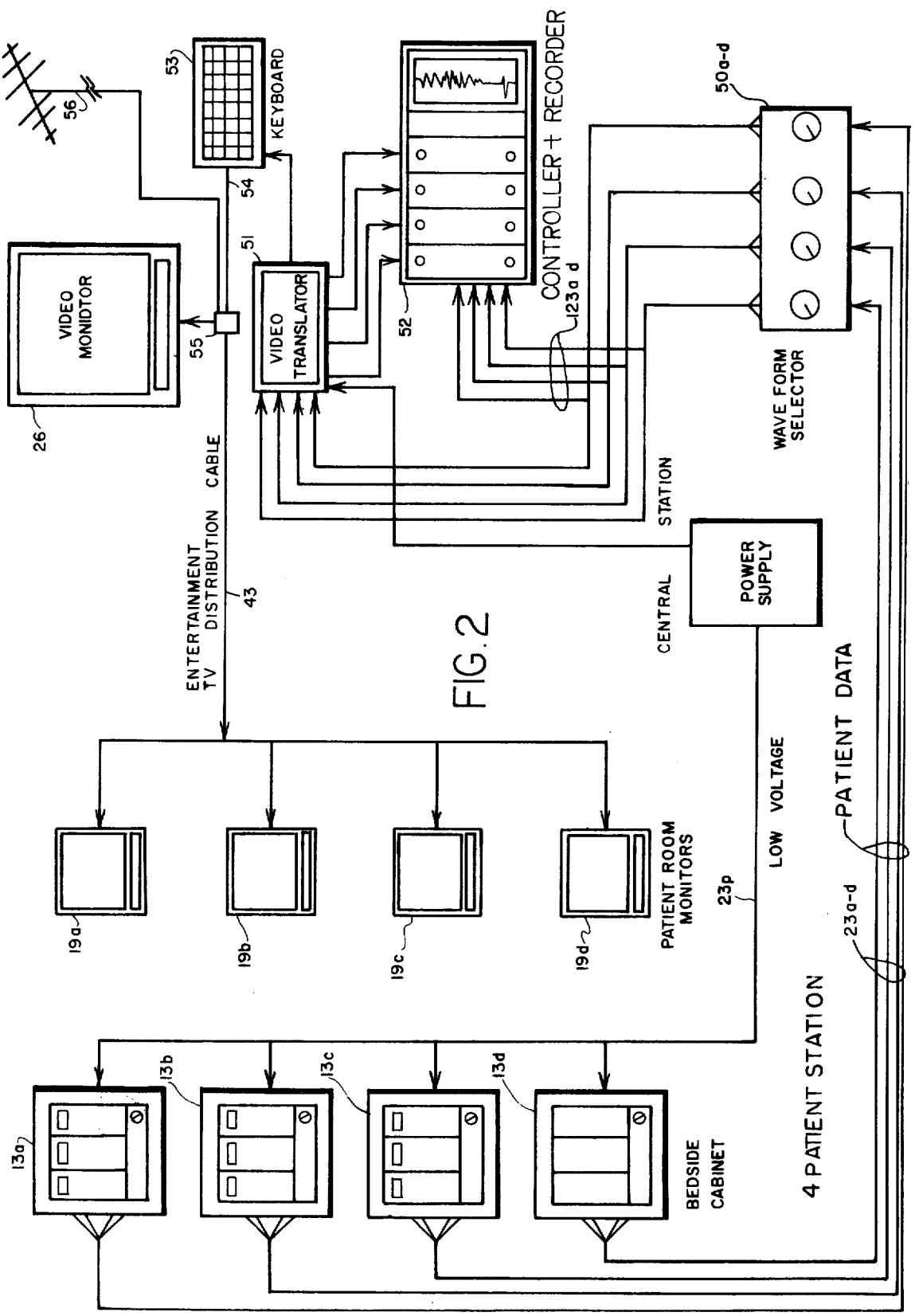
FIG. 2 is a simplified block diagram of this invention.

Now referring to FIG. 7, a typical patient station module is represented in this Figure. It is the pulse fail detector and pulse rate detector employing Wheatstone bridge sensor 300 of any of the several types available on the market, with two opposite junctions connected to a differential amplifier 301 and the opposite junctions connected between the regulated power supply from the central station identified as SUPPLY 302, and a voltage regulator 303 to ground. A zero calibrated switch 304 is associated with the sensor 300. The differential amplifier 301 is connected to an AF amplifier 305 with an RF bypass resistor 306 and gain set control 310. An automatic zero set circuit 307 controlled by local zero set switch 308 allows resetting to zero of the output any time by the person at the patient station. The zero set circuit may include an LED display 309 to indicate zero set condition. The output of the amplifier 305 is connected in parallel to each of four parallel stages 311 through 314. Stage 311 detects systolic rate. The stage 312 detects mean rate. Stage 313 detects diastolic rate and the stage 314 responds to the pulse rate. Selector switches 315, 316 and 320 are connected with each of the stages 311, 312 and 313, and the output of each of these is selectively connected via lead 321 to a BCD display 322 located at the patient station as illustrated in FIGS. 1 and 2. Output leads 323 from the BCD display 322 are connected via the cable 23 of FIG. 1 to the central control station for display and usage at the central console. The mean rate from stage 312 is also conveyed via lead 324 to an amplifier 325 and associated upper and lower limit stages 326 and 330, each of which are associated there with respective gates 331 or 332 and LED type visual indicators 333 and 334, which show deviations from preset limits by illumination of the appropriate LED. The output of the stages 326 and 330 also are connected to a common gate 335 with associated alarm 336 to give an alarm at any time either limit is exceeded. Actual pulse rate, in addition to being conveyed to the central station on lead 340 is amplified in amplifier 341 which drives an LED 342, for example green in color, to provide a visual indication of pulse rate. Each of the indicators of voltage supply present in the circuit in FIG. 1 are connected to appropriate leads from the central supply. No local supply is present.

FIG. 7 is representative of a typical patient module and, of course, different particular modules will be used for different parameters to be mentioned. Characteristically existing state of the art sensors are used and the information handing circuitry for making up the remainder of the module will be tailored to the sensor output and the characteristics needed to be displayed.

Figure 8:
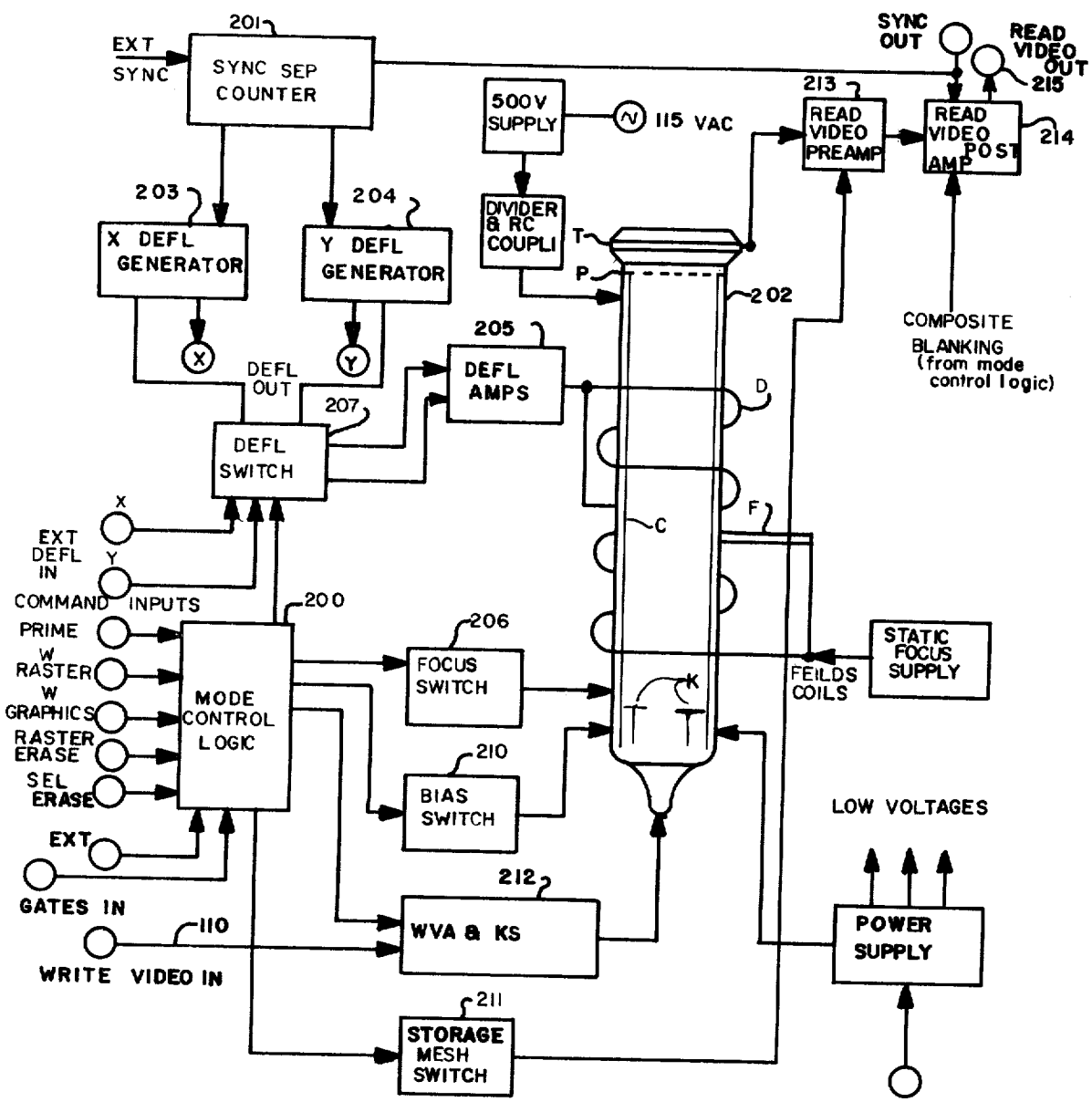
FIG. 8 is a block diagram of the video translator of the system of this invention.

Now referring to FIG. 8, the video translator 51 shown in block diagram form is an analog electrical signal storage unit with "nondestructive" readout. Analog input signals are introduced via lead 110 and routed to a scan converter tube 202, where they are "written" on the storage target T in the form of electrostatic charge potentials. Since the electron beam is projected along the "Z" (longitudinal) axis of the tube, the input signals, which control beam density, are referred to as Z, or Z-axis signals. The precise location on the storage target T to which the modulated electron beam is directed is governed by "X" (fast) and "Y" (slow) deflection signals applied to the electromagnetic deflection yoke D.

The analog input signals constituting the information to be stored may be fed to the video converter 50 in either a sequentially acanned or a selectively positioned format. As examples, the former deflection method would be a raster for accommodating television images as from channel 100, while the latter deflection method would be used to curve plots as from lead 110. The input deflection mode is selected by applying either a RASTER WRITE or a GRAPHICS WRITE command signal to the respective input terminals.

The key component upon which operation of video converter 51 depends is a scan converter tube 202, for example, Hughes Aircraft Company, Oceanside, California, Type H-1268. It is an electromagnetically focused and deflected cathode ray tube which functions in a manner analogous to that of the familiar picture tube, except that the electron beam is directed toward the charge-storage target T, rather than a phosphor viewing screen. The electron gun or K and deflection system are substantially the same as those employed in any high quality cathode ray tube. The operating modes of the scan converter tube 202 are WRITE, READ and ERASE (and PRIME, if required); these operating modes, and the methods by which they are carried out, are explained in detail in subsequent paragraphs.

The essential component parts of tube 202, shown in simplified form in FIG. 8, are the electron gun K, collimator C, collector P and storage target T, the latter two elements comprising the storage target assembly, plus the associated focus coil F and deflection yoke D. The metallic grid-like portion of the storage target is commonly referred to as the "storage mesh" (also as the "backing electrode") and, since output signals are taken from this tube element, it is designated the "signal output electrode."

The essential central elements of video translator 51 and the principal signal and power paths among them are shown in the functional block diagram, FIG. 8. For convenience of explanation, these elements are organized into five groups: (1) Timing circuits, (2) Deflection circuits, (3) Scan Converter tube electrode switching circuits (all electronic switching), (4) Video circuits, and (5) Power supplies, including the static focus current supply.

The timing circuits, by means of which the converter 51 carries out its prescribed writing (and priming), reading and erasing functions, at the proper times and for the proper durations, are comprised of the program section which includes control logic circuitry 200 and the Sync Separator/Counter 201. The Sync Separator 201 is active when externally supplied composite 525-line 60 Hz or 625-line 50 Hz sync is used; under this condition, the internal counter is disabled. Otherwise, the Unit is synchronized by the internal 525-line 60 Hz line-locked counter.

Deflection circuits, which govern the scanning pattern and sweep rate of a scan converter tube 202 electron beam consist essentially of the X and Y deflection generators 203 and 204, and their associated deflection amplifiers 205.

The tube electrode switching circuits change scan converter tube 202 operating conditions in accordance with incoming mode commands: RASTER WRITE, GRAPHICS WRITE, RASTER ERASE, SELECTIVE ERASE, and when used, PRIME. In the absence of any of these commands, the circuits automatically switch operating conditions of the scan converter tube 202 to READ mode. Switching signals, derived from mode command signals in the program section are routed to five switching circuits: (1) Focus switch 206, (2) Deflection switch 207, (3) Bias switch 210, (4) Storage mesh switch 211, and (5) the Write video amplifier and cathode switch 212.

The focus switch 206 changes the d.c. voltage of the electrode of the tube 202 in the WRITE and SELECTIVE ERASE modes. By means of this small correction in writing and selective erasing, optimum beam focus is maintained in all modes.

The deflection switch 207 effects prescribed changes in scan converter tube 202 beam scanning for the various modes. For example, if externally deflected writing and internally deflected reading are used, the deflection switch 207 connects signal paths from the external deflection input terminals to the deflection amplifiers 205 in the WRITE mode, and from the internal X and Y deflection generators 203 and 204 to the deflection amplifiers 205 in READ mode. Deflection switching is required wherever scanning schemes differ with respect to format, scanning axis, scanning rate or polarity.

Since, among the various modes, the scan converter tube 202 is operated at several different electron beam energy levels, a means is required to establish optimum beam intensity for each mode. This requirement is met by changing control grid bias levels, a function carried out by the bias switch 210.

The storage mesh switch 211 and the cathode switch 212, which latter is an integral part of the write video amplifier, act in concert to set the scan converter tube 202 electron beam level corresponding to a particular mode command. The storage mesh switch 211 effects appropriate changes in the storage mesh of the tube 202 (also referred to as "backing electrode") d.c. operating level and, at the same time, the cathode switch places the proper d.c. voltage on the converter tube 202 cathode. Additionally, the write video amplifier 212 is enabled only in the RASTER WRITE, GRAPHICS WRITE and when used, PRIME modes. Beam modulation is applied in the WRITE modes but not in PRIME mode.

Video Circuits include the write video amplifier 212, read video preamplifier 213, and read video post amplifier 214. The write video amplifier 212 raises input video amplitudes to proper levels for application to the scan converter tube 202, while the post amplifier 214 adds sync and blanking signals to the video, and mades the composite signal available to READ VIDEO OUTPUT Jack 215.

For a more complete explanation of the operation of the Hughes Type Scan Converter, reference should be made to the Instruction Manual of Model MSC-1, available from the Hughes Aircraft Company, Industrial Products Division, Oceanside, Calif.

The above described embodiments of this invention are merely descriptive of its principles and are not to be considered limiting. The scope of this invention instead shall be determined from the scope of the following claims, including their equivalents.

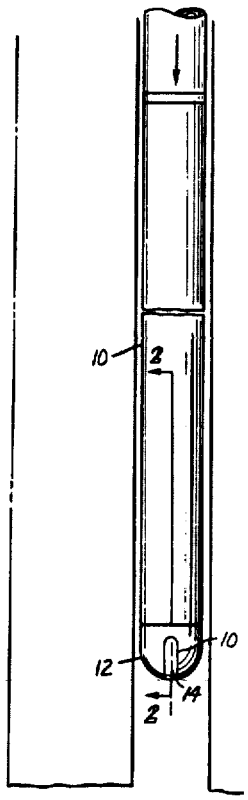

What is claimed is:

1. A patient monitoring system comprising a central control console including:
    a. a power supply;
    b. a controller for establishing alarm limits for patient data;
    c. a video translator for converting patient analog date into video traces representative of the analog values thereof;
    d. keyboard means for generating alpha numeric data;
    e. means for combining alpha numeric data with said video traces of patient analog data;
    f. means for introducing said combined data into a television distribution medium;
        at least one patient station including means connectable to patient sensor for amplifying a patient parameter sensor to a predetermined level;
        said amplifying means powered by said power supply of said central control console;
        means conducting said amplified parameter to said central control console;
    wherein said video translator includes means for storing analog patient data for a selected period of time and for introducing said data into said distribution system at the end thereof; and
    wherein said video translator includes means for establishing a WRITE and an ERASE cycle, including switch means for temporarily terminating the WRITE and ERASE cycle of said video translator and for enabling said recorder to record the analog data stored in said video translator.

2. The combination in accordance with claim 1 wherein said console includes an R.F. receiver and wherein said switch means is responsive to signals detected by said R.F. receiver and portable R.F. transmitter for generating and transmitting a signal to said R.F. receiver.

3. A patient monitoring system comprising a central control console including:
    a. a power supply;
    b. a controller for establishing alarm limits for patient data;
    c. a video translator for converting patient analog data into video traces representative of the analog values thereof;
    d. keyboard means for generating alpha numeric data;
    e. means for combining alpha numeric data with said video traces of patient analog data;
    f. means for introducing said combined data into a television distribution medium;
        at least one patient station including means connectable to a patient sensor for amplifying a patient parameter sensor to a predetermined level;
        said amplifying means powered by said power supply of said central control console;
        means conducting said amplified parameter to said central control console;
    wherein said video translator includes means for storing analog patient data for a selected period of time and for introducing said data into said distribution system at the end thereof; and
    wherein said video translator includes means for varying the horizontal sweep rate of said analog data stores therein.

4. A patient monitoring system comprising:
    a patient station including a recessed wall mounted console;
    said console including a plurality of amplifiers and connector means for said amplifiers to interconnect said amplifiers to patient sensors;
    a central control console located remote from said patient station;
    said central control station including power supply means for operating said amplifiers;
    cable means for supplying power from said control console to said amplifier means and to conduct physiological signals from said amplifiers to said central control console;
    means at said central control station for translating physiological signals received from said patient station into video format;
    means for generating alpha numeric information;
    means combining video formatted physiological information with alpha numeric information into a display with each visually associated together and means for conducting said combined display to at least one television monitor;
    including printing means including a second monitor, said printing means responsive to command to print a copy of the information displayed on said second monitor; and
    switch means for commanding the operation of said printing means.

5. The combination in accordance with claim 4 wherein said switch means comprises;
    a switch connected to said printing means;
    a video frequency receiver connected to operate said switch upon receipt of a command signal; and
    a portable radio frequency transmitter for generating such command signal.

* * * * *

United States Patent [19]
Laikin et al.

[11] 4,051,523
[45] Sept. 27, 1977

[54] SUBMERSIBLE CAMERA

[75] Inventors: Milton Laikin, Los Angeles; George L. Hatchett, El Cajon, both of Calif.

[73] Assignee: Hydro Products, Inc., San Diego, Calif.

[21] Appl. No.: 593,116

[22] Filed: July 3, 1975

[51] Int. Cl.² .......................................... H01J 29/89
[52] U.S. Cl. ................................ 358/99; 358/225
[58] Field of Search ............ 178/7.82, 7.85, DIG. 37, 178/DIG. 38, 7.87, 7.88, 7.2; 176/6.8

[56] References Cited
U.S. PATENT DOCUMENTS

| 2,849,530 | 8/1958 | Fleet | 178/DIG. 1 |
| 2,905,758 | 9/1959 | Walker | 178/7.2 |
| 3,780,224 | 12/1973 | Levine | 178/7.85 |

*Primary Examiner*—Robert L. Griffin
*Assistant Examiner*—Michael A. Masinick
*Attorney, Agent, or Firm*—Fulwider, Patton, Rieber, Lee & Utecht

[57] ABSTRACT

A closed circuit television camera intended to be lowered into a body of water to inspect articles within the water. The camera has a lens capable of movement of 90° each side of its normal axis, thus permitting the camera to scan an angle of 180° from one side to the other.

7 Claims, 8 Drawing Figures